United States Patent [19]

Akiyama

[11] Patent Number: 4,483,688
[45] Date of Patent: Nov. 20, 1984

[54] CATHETER

[76] Inventor: Hiroshi Akiyama, 2-5-12, Honkomagome, Bunkyo-ku, Tokyo, Japan

[21] Appl. No.: 470,690

[22] Filed: Feb. 28, 1983

Related U.S. Application Data

[63] Continuation-in-part of Ser. No. 189,244, Sep. 22, 1980, abandoned, which is a continuation-in-part of Ser. No. 923,440, Jul. 10, 1978, abandoned, which is a continuation-in-part of Ser. No. 740,285, Nov. 9, 1976, abandoned.

[51] Int. Cl.³ .......................................... A61M 25/00
[52] U.S. Cl. .................................... 604/265; 604/326
[58] Field of Search ................ 604/265, 266, 326, 327

[56] References Cited

U.S. PATENT DOCUMENTS

3,396,727  8/1968  Mount ............................. 604/265 X
3,699,956 10/1972  Kitrilakis et al. ............... 604/265 X
3,848,603 11/1974  Throner ............................ 604/265 X
4,054,139 10/1977  Crossley ............................. 604/265

Primary Examiner—Dalton L. Truluck
Attorney, Agent, or Firm—Jordan and Hamburg

[57] ABSTRACT

A combination catheter and drainage system includes a flexible tubular member oligodynamically treated in part and having an aperture adjacent said one end to allow communication between a main lumen and the exterior of the tubular member, a balloon being provided adjacent the aperture and an auxiliary lumen being connected to the main lumen for inflating the balloon and a urine collecting bag connected to the tubular member via a connector means which is oligodynamically treated. The collecting bag is also provided at its discharge distal end with an oligodynamically active metal device thereby forming a system which is completely closed against entry of ambient microorganisms.

15 Claims, 12 Drawing Figures

CATHETER

CROSS-REFERENCES TO RELATED APPLICATIONS

This application is a continuation-in-part of my copending application Ser. No. 189,244 filed Sept. 22, 1980, now abandoned, which is a continuation-in-part of my application Ser. No. 923,440 filed July 10, 1978, now abandoned, which is a continuation-in-part of my application Ser. No. 740,285 filed Nov. 9, 1976, now abandoned.

BACKGROUND OF THE INVENTION

1. Field of the Invention

The present invention relates to a catheter and drainage system and more particularly to improvements therein whereby bacterial intrusion into the system is effectively barred.

2. Prior Art

As is well known, the patients who have suffered from cerebrospinal diseases such as cerebral hemorrhage, softening of brain or spinal injuries, tend to be afflicted with dysuria of incontinence of urine. It is therefore necessary in such instance that a urinary catheter be inserted into the urethra and retained in the appropriate position for urination for such patients as well as for those who have undergone various surgical operations. Such catheters are often called "indwelling catheters," which must be sufficiently mechanically soft and resilient for effective use.

While the indwelling catheter is retained in the urethra for a relatively long period of time, it would permit pathogenic bacteria attached to the anus or genital vulva to enter through the urethra into the bladder, thereby frequently causing cystitis, urethritis, or pyelitis or the so-called "ascending infection." This is pronounced particularly with female because her urethra is wider, shorter, and more linear than that of male.

Various attempts have been made to prevent the bacterial infection during the use of such indwelling catheters. One such attempt has been to coat the catheter with an ointment containing an antibiotic or bactericide. Another attempt has been to irrigate the bladder through the catheter and wash the catheter at frequent intervals, and at the same time to administer the patients with antibiotics for prophylactic purposes. These proposals, however, are tedious and time-consuming, and are not completely free from renewed invasion by pathogenic bacteria.

Indwelling catheters are nowadays used in combination with urine drainage devices of either an open-circuit or closed circuit design. The closed drainage system has been preferred to delay infection in patients with long-term urethral catheterization by virtue of its isolation from the ambient. Reportedly, however, more than 60 percent of the patients catheterized in closed drainage systems are infected within about seven days due to intrusion of bacterial from between an exposed portion of the catheter and the mucous membrane of the urethra, between the catheter and the drainage tube, or from the outlet of the urine collecting bag.

SUMMARY OF THE INVENTION

The present invention seeks to provide an improved indwelling catheter which will prevent urinary tract infections or ascending infection due to pathogenic bacteria while the catheter is being used.

According to an important aspect of the invention, there is provided a combination catheter and drainage system of a closed design for infection-free long-term catheterization. The indwelling catheter provided in accordance with the invention comprises a flexible tubular member having a main lumen for urine discharge, one end of the main lumen being closed by a tip, the tubular member having an aperture adjacent said one end to allow communication between the main lumen and the exterior of the tubular member, and a balloon provided adjacent the aperture, an axillary lumen connected to the main lumen for inflating the balloon, an oligodynamically active metal deposited on the periphery of the tubular member for producing metal ions upon contact with the urine.

The oligodynamic metal used in accordance with the invention is typically a heavy metal such as copper, silver, gold or their alloys including intermetallic compounds thereof. It has now been found that these metals exert in the form of metal ion concentrations only of the order of about $1 \times 10^{-6}$M a profound bactericidal effect.

According to another important aspect of the invention, the indwelling catheter is applied with an oligodynamically active coating only at its outside periphery, whereby the outside diameter of the catheter tube per se can be reduced to a minimum with the inside diameter maintained at a maximum to provide comfortable catheterization and smooth and effective drainage of urine.

Prior art counterparts are coated on both the outside and inside surfaces of the catheter tube and hence have a drawback in that the tube is necessarily smaller in inside diameter for a given outside diameter and susceptible to inner surface irregularities due to coating with the result that not only the flow of urine is retarded or otherwise blocked but also such coated interior can become a site for bacterial growth.

According to a preferred embodiment of the invention, the coated catheter is connected to a urine collecting bag having a drain pipe by means of a connector fitted between a flared outlet end of the catheter and a drainage tube leading to the bag, the connector and the drain pipe being also plated or coated with an oligodynamic metal. This arrangement ensures oligodynamic protection against urinary tract infections at all points of origin that may be disposed for contact with the ambient atmosphere.

The invention will now be described in greater detail, by way of example, with reference to the drawings, in which like reference characters refer to like and corresponding parts throughout the several views and in which:

DETAILED DESCRIPTION OF THE PREFERRED EMBODIMENTS

Figure 1:
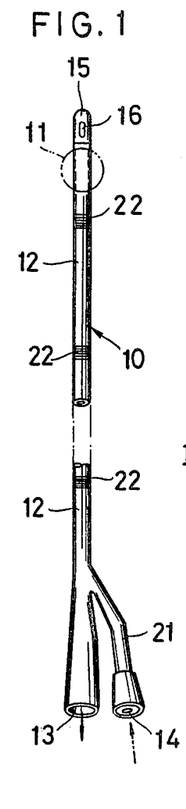
FIG. 1 is a fragmentary plan view of a catheter equipped with an anchoring balloon.
Figure 2:
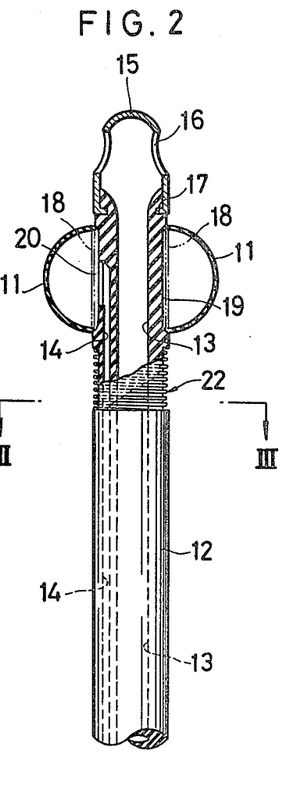
FIG. 2 is an enlarged, partly cross-sectional view of the catheter shown in FIG. 1.
Figure 3:
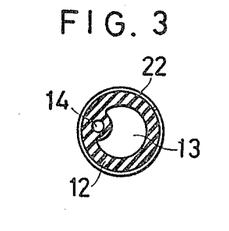
FIG. 3 is a cross-sectional view taken along the line III—III of FIG. 2.

Reference to FIGS. 1 to 3 inclusive shows a urethral catheter 10 equipped with an anchoring balloon 11. The balloon catheter 10 comprises a tube 12 made of rubber or plastics having a main lumen 13 and an auxiliary or inflation lumen 14 attached to the wall of the primary lumen 13. One end of the tube 12 is closed by a cap 15 made of copper or silver and having a hole 16 through which urine is taken into the main lumen 13. The cap 15 has on its bottom end a circular flange 17 fitted in the tube 12. Alternatively, the cap 15 may be integral with the tube 12. A balloon-forming layer 18 is provided beneath the cap 15 and over a recess 19 in the exterior surface of the tube 12. An aperture 20 is formed in the tube wall to provide communication between the inflation lumen 14 and the exterior recess 19. The inflation lumen 14 extends along the tube 12 and is branched off to be connected to an inflation tube 21. A suitable inflation medium is injected from the inflation tube 21 through the inflation lumen 14 and through the aperture 20 to expand the layer 18 to a balloon-like configuration as shown in FIG. 2. For discharge of urine, the main lumen 13 is open at a flared end of the tube 12 opposite to the distal end where the cap 15 is located. Beneath the balloon layer 18, an oligodynamically active metal coil 22 measuring about 0.05 to 0.5 mm in diameter is wrapped around the tube 12. Similar coils 22 are provided at spaced intervals along the length of the tube 12. These coils must be embedded to keep their outer peripheral surfaces lying substantially flush with the exterior surface of the tube 12.

Figure 5:
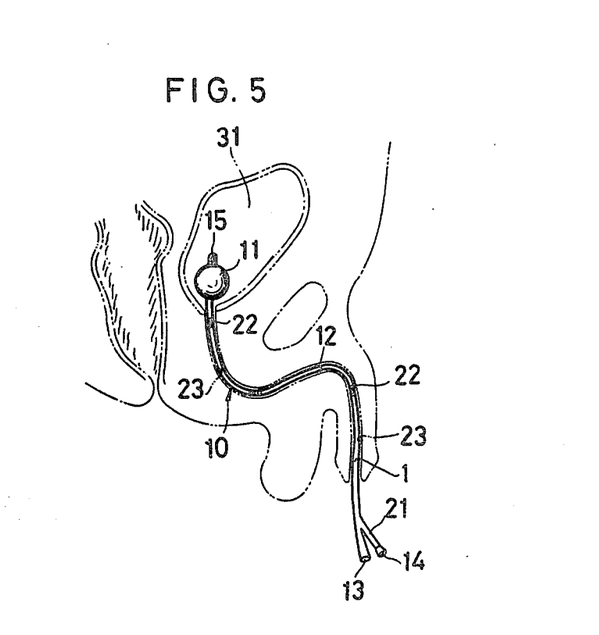
FIGS. 5 and 6 are schematic views illustrating the manner in which the balloon catheter is inserted in the male's and the female's urethra, respectively.
Figure 6:
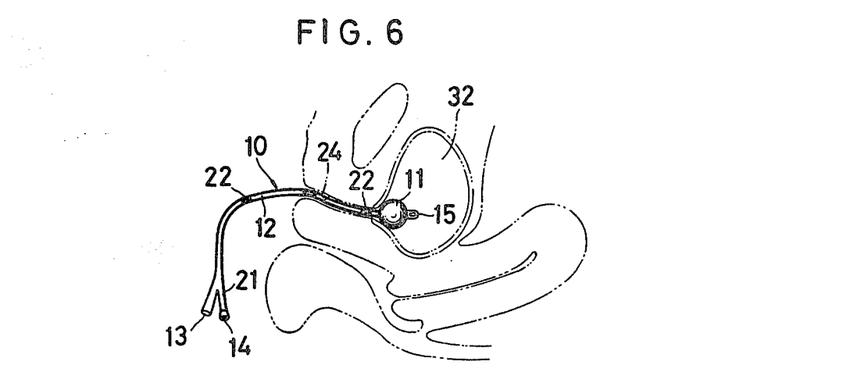

In use the balloon catheter 10 is inserted into the male's urethra 23 or female's urethra 24, and an inflation medium is pumped through the inflation lumen 14 to expand the anchoring balloon 11, as illustrated in FIGS. 5 and 6. This prevents accidental disengagement of the catheter 10 from the patient and anchors the catheter 10 in the appropriate position for efficient use. With the catheter 10 thus anchored in the urethra, urine can be drained from the bladder 31 or 32 through the main lumen 13. When the catheter is no longer needed, the balloon 11 is deflated by releasing the inflation medium and the catheter 10 is removed from the patient.

Figure 4:
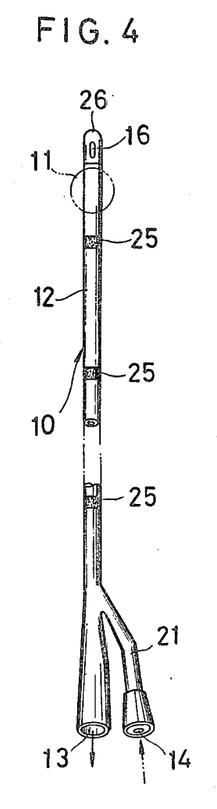
FIG. 4 is a plan view of a catheter according to another embodiment of the invention.

The embodiment shown in FIG. 4 is characterized by the application to the exterior of the tube 12 of a silver or other oligodynamically active metal in a powdery form ranging in particle size between 200 and 300 mesh. The metal powder is dispersed in suitable binders and coated on a portion of the outer peripheral surface of the tube 12 at spaced intervals along the length thereof as at 25 corresponding in position to the coils 22 of the catheter 10 shown in FIG. 1, the oligodynamically treated areas being determined by the length of the male or female urethra. The catheter 10 shown in FIG. 4 has a rounded tip 26 of rubber or plastic similar to the material of the tube 12 and is devoid of the metal cap 15.

The embodiment in which the oligodynamic coating 25 is applied in lieu of the coil 22 is preferred because the coating 25 being applied to a minimum thickness retains flexibility of the tube 12 to provide more comfortable catheterization especially for long-term patients taking into account the fact that the mucous membrane of the urethra is extremely sensitive to inflation, irritation or foreign matters. For comfortable usage, the catheter 10 should be as small in outside diameter as possible. At the same time, its inside diameter should be large enough to maintain smooth flow and drainage of urine. This dual feature is achieved by the concept of applying the oligodynamic coating only to the outside surface of the tube 12 while the inside of the tube 12 is left intact. The thickness to which the coating 25 is applied may be of the order of 300–600 microns.

It is reported that a grown-up male in health urinates over twenty four hours an average of 1,000–1,500 c.c. of water and 55–70 grams of solids, but patients' urine contains considerable waste materials that are sedimented or deposited, or crystallized medicaments. Hospitalized patients' smooth muscles do not function properly for urination and therefore rely on the gravity of flow, for which purpose the inner periphery of the tube 12 should be smooth and free of irregularities which would otherwise result from coating or other treatment of the interior of the tube 12.

Figures 7, 8:
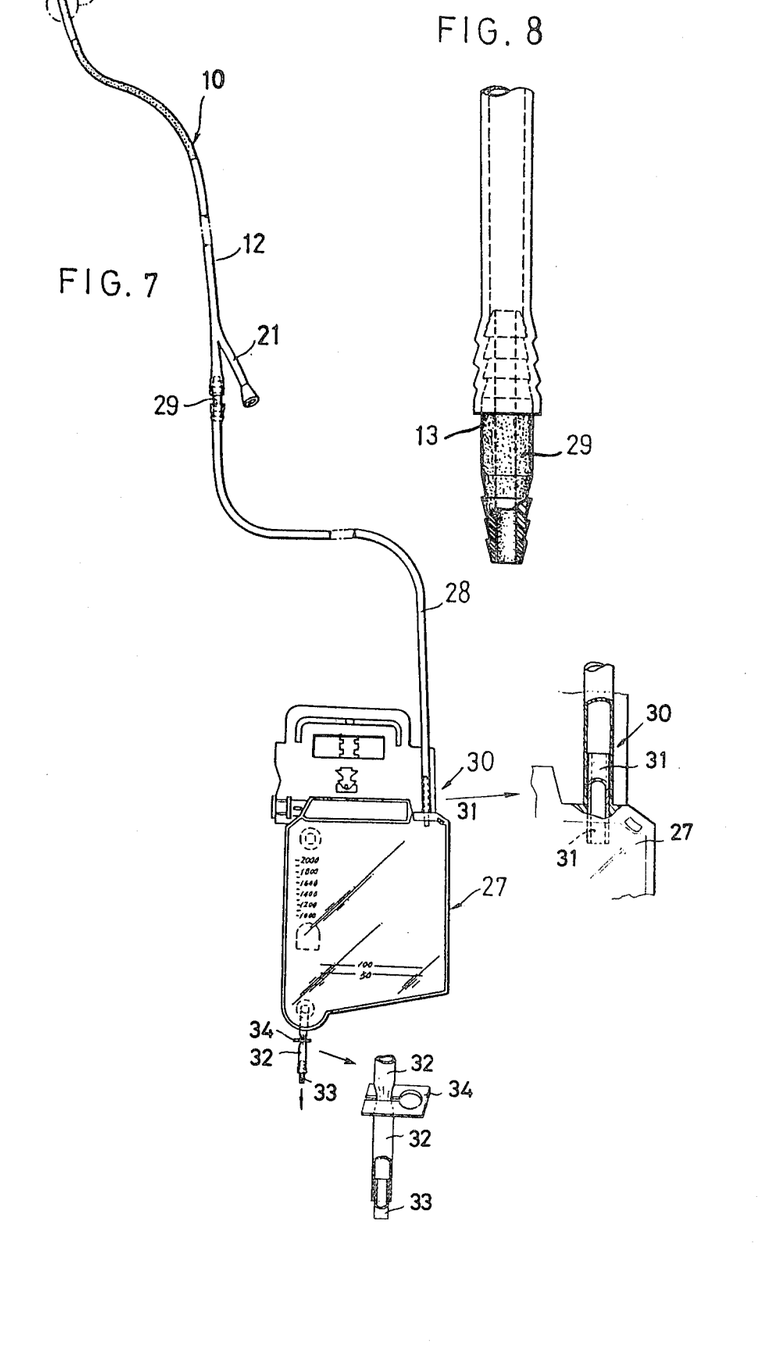
FIG. 7 is a plan view of the balloon catheter of FIG. 1 (or FIG. 4) shown as connected to a urine collecting bag.
FIG. 8 is a plan view of a connector adapted to connect the catheter to a drainage tube.

In indwelling urethral catheterization, the catheter 10 is connected to a urine collecting bag 27 via a drainage tube 28 to permit uninterrupted drainage of urine from the patient as shown in FIG. 7. A connector 29 is adapted to join the flared outlet end of the tube 12 to one end of the drainage tube 28, the other end of this tube being connected via a connector 30 to the bag 27. The connector 29 may be of any known form and construction, an example being shown in FIG. 8. Importantly, the connector 29 according to the invention is plated or coated with silver or other oligodynamically active metals to provide an effective barrier against intrusion of ambient infecting organisms from the junction into the urinary tract and up towards the bladder. The junction 30 between the drainage tube 28 and the bag 27 is provided with a pipe 31 made of copper which also has an oligodynamic activity for eliminating bacteria that may ascend from the bag 27. The urine collecting or drainage bag 27 is well known and shown as a closed drainage system which is preferred over an open system in recent years to delay infection in patients with long-term urethral catheterization.

At the bottom of the bag 27 is provided a discharge outlet 32 which is attached with a clamp 34 and also connected to a copper pipe 33 capable of oligodynamically preventing entry of bacteria from the ambient atmosphere.

EXAMPLE

A balloon catheter 10 was coated with silver particles of about 300 mesh over a length of 55 to 60 mm at a position about 5 mm below the lower end of the balloon 11. These catheters each connected via connector 29 to a urine collecting bag 105 of an open drainage system (FIG. 12) were used in a total of 102 patients (40 males and 62 females) hospitalized at St. Lukes' International Hospital in Tokyo for bladder catheterization after surgical operations or in those with urinary retention for periods ranging from 4 to 77 days. No antibiotic therapy was administered except for pneumonia for 2 cases over a short period of time. All the cases ranging in age from 18 to 80 were free of urinary bacteria prior to the use of the inventive system. For long-term catheterization, the replacement of new system sets was made every 7 days. Urine was sampled with a needle through sterilized spot of the catheter in an open drainage system. Initially, urine samples were cultured daily but since the cultures done for a week were negative for bacteria in the first 5 cases they were done at intervals of 2 days to a week in the remaining patients. Quantitative urine cultures were done using heart infusion agar plates that were incubated at 37° C. for 48 to 72 hours. During the period of indwelling catheterization, no antibiotics, as a rule, were administered but no patient developed over bacteriuria (over $10^5$ bacteria per ml) or symptoms of urethritis.

In contrast, all of 20 patients in the control group who had indwelling catheters of conventional type developed bacteriuria with 4 days of catheterization.

The data obtained and shown in Tables 1 and 2 indicate that effective prevention of urinary tract infection which is frequently associated with indwelling urethral catheterization can be achieved by the use of the catheter and drainage system provided in accordance with the invention.

RESULTS

The ages of the 102 patients ranged from 18 to 80 years. During catheterization none had bacteriuria (defined as containing a minimum of $10^5$ bacteria per ml.) (Tables 1 and 2) or pyrexia more than 38.5° C. Of the patients 62 percent showed an increase in temperature to 38.0° C. 1 or 2 days after catheterization, possibly owing to the influence of the preceding operation. In no case were there symptoms or signs of acute urethritis frequently associated with indwelling catheterization, that is urethral discharge, a constant itching or burning sensation in the urethra, and reddening and edema of the external meatus. Followup 1 to 4 months after removal of the catheter revealed no significant adverse findings in any of the 102 cases studied.

In contrast, all of the 20 control patients had bacteriuria within 4 days (mean 48 hours) of indwelling catheterization. Pyrexia more than 38.5° C. occurred in 5 cases (25 percent), urethral discharge in 15 (75 percent), itching or burning sensation in the urethra in 4 (20 percent) and reddening and edema of the external meatus in 2 (10 percent).

TABLE 1

Cases of Prolonged Catheterization

| Case | Age | Clinical diagnosis | Operation | Duration of catheterication (days) | Fever (38.5° C.) | Antibiotics | Symptoms of urethritis | Bacteriuria* |
|---|---|---|---|---|---|---|---|---|
| 1 | 79 | (1) Encephalomalacia (2) Compression fracture of $Th_{12}$ and $L_3$ | | 77 | + (pneumonia) | + (for pneumonia) | — | — |
| 2 | 43 | (1) Pelvic endometriosis (2) Teratoma of rt. ovary | Abdominal hysterectomy + bilateral adnexectomy | 9 | — | — | — | — |
| 3 | 32 | Cervical incompetency | Schirodkar's operation | 8 | — | — | — | — |
| 4 | 65 | Apoplexy | | 15 | — | — | — | — |
| 5 | 52 | Hemiplegia | | 25 | — | — | — | — |
| 6 | 55 | Adenocarcinoma of Lt. ovary | Abdominal hysterectomy + bilateral adnexectomy | 10 | — | — | — | — |
| 7 | 68 | (1) Prolapsus uteri (2) Arthritis deformans | Abdominal hysterectomy | 11 | — | — | — | — |

*over $10^5$ bacteria per ml.

TABLE 2

Comparison of clinical effects of catheterization with inventive type and conventional catheter

| | | Type of catheter | |
|---|---|---|---|
| | | Inventive (102 cases) | Conventional (20 cases) |
| Duration of catheterization (days) | | 4–77 | 3–4 |
| Bacteriuria (over $10^5$ bacteria per ml) | | none | 20 (within 4 days, average 2 days) |
| Fever (38.5° C. ↑) | | none | 5 |
| Symptoms of urethritis | Urethral discharge | none | 15 |
| | Itching or burning sensation | none | 4 |
| | Reddening or edema of external meatus | none | 2 |

Figure 12:
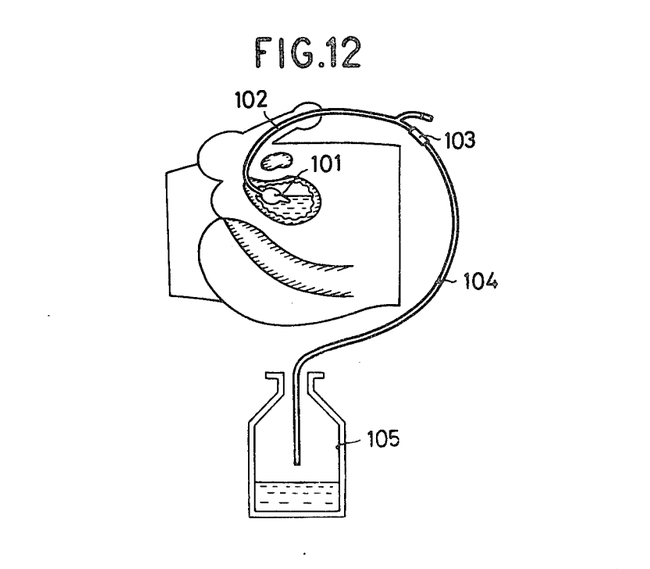
FIG. 12 is a schematic view of a prior are catheter and drainage system.

The tabulated results were obtained with use of the conventional open drainage system typically shown in FIG. 12, in which reference numeral 101 corresponds to part 11; reference numeral 102 to part 12; reference numeral 103 to part 29; reference 104 to part 28; and reference numeral 105 designates an open-type drainage bag. The illustrated system is literally open for intrusion of bacterium from the exposed area, and the bacteria ascend after being cultured in the bag or directly through the drainage tube. The interior of the bag or the tube is moist and becomes a site for rapid bacterial growth which is known as "doubling" which takes place about every 20 minutes.

Figure 11:
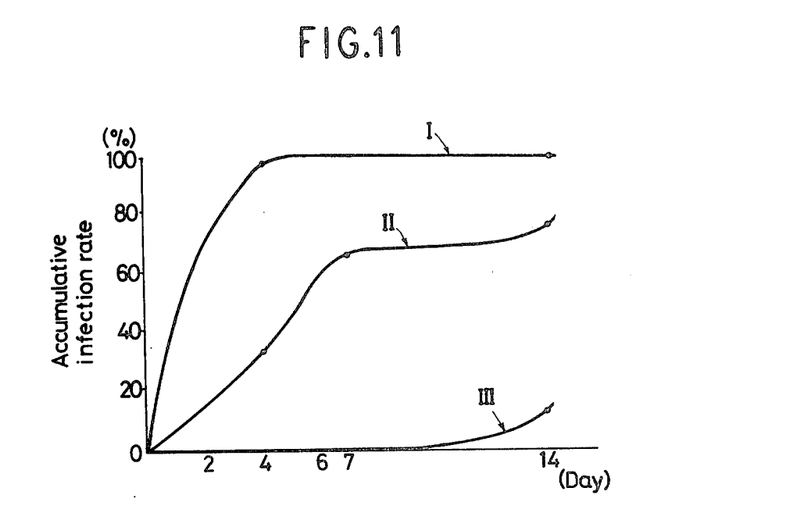
FIG. 11 is a graph illustrating the performance curve of the invention as against that of the prior art counterpart.

Referring now to FIG. 11 which graphically illustrates the risks of bacteriuria, the curve I represents the result of the open drainage system in which 100 percent of the patients showed the symptom of urinary tract infection within 4 days. The curve II represents the result of the conventional closed drainage system in which 30 percent of the patients were found infected within 4 days and 60 percent within 7 days. In contrast to these conventional systems, the improved closed catheter and drainage system according to the invention showed no appreciable signs of infection even after 10 days of catheterization as represented by the curve III.

Figure 9:
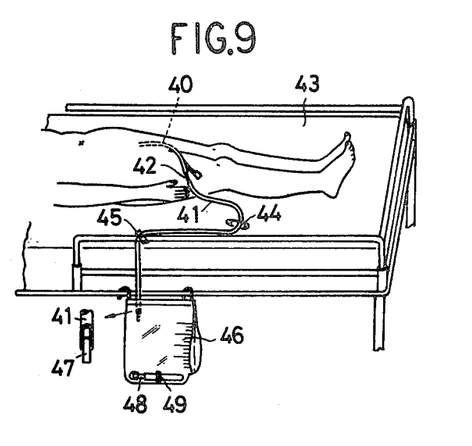
FIG. 9 is a schematic view utilized to explain the manner in which a patient lying on bed is being catheterized in accordance with the principles of the invention.

In practice, the inventive system may be applied to a patient lying on bed 43 in a manner illustrated in FIG. 9, in which reference numeral 40 corresponds to part 10; reference numeral 41 to part 28; reference numeral 42 to part 29; reference numeral 46 to part 27; reference numeral 47 to part 31; reference numeral 48 to part 33; and reference numeral 49 to part 34. The drainage system in FIG. 9 is shown secured to the bed 43 with the drainage tube 41 pinned as at 44 and taped as at 45.

Figure 10:
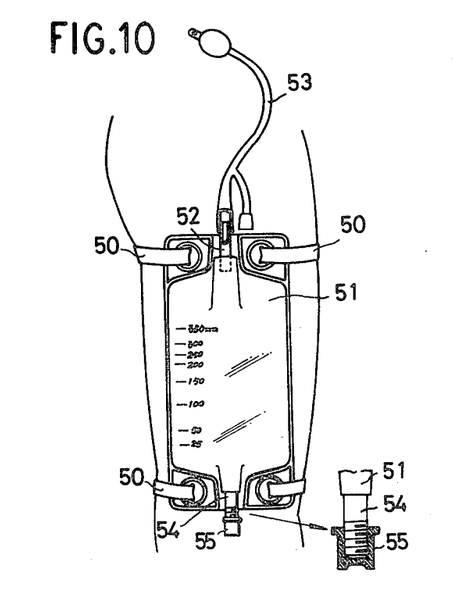
FIG. 10 is a schematic view utilized to explain the manner in which the system of the invention is applied to a pedestrian patient.

Alternatively, the system may be attached to the thigh of a pedestrian patient in a manner shown in FIG. 10, in which reference numeral 51 corresponds to part 27; reference numeral 52 to part 31; reference numeral 53 to part 12; and reference numeral 54 to part 33. In this embodiment, the bag 51 is attached to the thigh of the patient by means of tapes or bands 50 to allow him to walk with the system on. Designated at 55 is a socket threadedly engaged with the pipe 54.

In either of the embodiments shown in FIGS. 9 and 10, the important concept underlying the invention is embodied in which all possible sources of entry of ambient bacteria as at 42, 47 (52), and 48 (54), are covered by oligodynamically active means to protect the patient against urinary tract infection.

Although various minor modifications may be suggested by those versed in the art, it should be understood that I wish to embody within the scope of the patent warranted hereon, all such embodiments as reasonably and properly come within the scope of my contribution to the art.

What is claimed is:

1. A catheter and drainage system for draining urine from a body cavity comprising, in combination, an indwelling catheter, said catheter comprising a flexible tubular member having a main lumen for urine discharge, one end of said main lumen being closed, said tubular member having an aperture adjacent to said one end to allow communication between said main lumen and the exterior of said tubular member, a balloon provided adjacent said aperture, an auxiliary lumen connected to said main lumen for inflating said balloon, and an oligodynamically active metal deposited on a portion of only the outside periphery of said tubular member for producing metal ions upon contact with the urine; a draining tube, a connector means connecting said main lumen to said drainage tube, said connector means having an oligodynamically active metal providing a barrier against intrusion of ambient organisms into said drainage tube, a urine collecting bag having an inlet, and a tubular sterilizing means having oligodynamic activity connecting said drainage tube to said inlet of said collecting bag.

2. A catheter and drainage system as defined in claim 1 wherein said oligodynamically active metal is one selected from the group consisting of silver, gold, copper and their alloys.

3. A catheter and drainage system as defined in claim 1 wherein said tubular member is coated with less than 300 mesh particles of an oligodynamically active metal at spaced intervals along its length.

4. A catheter and drainage system as defined in claim 1 wherein one end of the main lumen is closed by a cap made of an oligodynamically active metal.

5. A catheter and drainage system as defined in claim 1 wherein said portion is disposed on said tubular member adjacent to said balloon.

6. A catheter and drainage system as defined in claim 1 wherein said portion is disposed on said tubular member about 5 mm from said balloon.

7. A catheter and drainage system as defined in claim 1 wherein said portion has an axial length of about 55 to 60 mm.

8. A catheter and drainage system as defined in claim 1 wherein one end of the main lumen is closed by a cap plated with an oligodynamically active metal.

9. A draining system for conducting draining body fluids from an insertable device extending partially into a body cavity to be drained to a drainage bag, the combination comprising a catheter tube coated with an oligodynamically active metal only on the outside periphery for producing metal ions upon conact with said body fluids, a drainage tube, a connector means connecting said catheter tube to said drainage tube, said connector means having an oligodynamically active metal to provide a barrier against intrusion of ambient infecting organisms into said drainage tube, and a drainage bag having an inlet, said drainage tube being connected to said inlet of said drainage bag.

10. A draining system for conducting draining body fluids from an insertable device extending partially into a body cavity to be drained to a drainage bag, the combination comprising a catheter tube coated with a oligodynamically active metal only on the outside periphery for producing metal ions upon contact with said body fluids, a drainage tube, a connector means connecting said catheter tube to said drainage tube, a drainage bag having an inlet, and an oligodynamically active tubular member connecting said drainage tube to said inlet of said drainage bag, said oligodynamically active tubular member precluding bacteria from ascending from said drainage bag.

11. A draining system according to claim 10 wherein said oligodynamically active tubular member comprises a connector having an oligodynamically active metal deposited on the outside surface thereof to provide a barrier against intrusion of ambient infecting organisms into said drainage tube and up toward the body cavity.

12. A draining system according to claim 10 wherein said olibodynamically active tubular member is a pipe made of copper.

13. A draining system for conducting draining body fluids from an insertable device extending partially into a body cavity to be drained to a drainage bag, the combination comprising a catheter tube coated with an oligodynamically active metal only on the outside periphery for producing metal ions upon contact with said body fluids, a drainage tube, a connector means connecting said catheter tube to said drainage tube, a drainage bag having an inlet and an outlet, said drainage tube being connected to said inlet of said drainage bag, and an oligodynamically active tubular member connected to said outlet of said drainage bag and oligodynamically preventing entry of bacteria from the ambient atmosphere.

14. A draining system according to claim 13 wherein said oligodynamically tubular member is a pipe made of copper.

15. A draining system for conducting draining body fluids from an insertable device extending partially into a body cavity to be drained to a drainage bag, the combination comprising a catheter tube coated with an oligodynamically active metal only on the outside periphery for producing metal ions upon contact with said body fluids, a drainage tube, a connector means connecting said catheter tube to said drainage tube, said connector means having deposited at least on the outer periphery thereof an oligodynamically active metal to provide a barrier against intrusion of ambient infecting organisms into said drainage tube, a drainage bag having an inlet and an outlet, a first oligodynamically active tubular member connecting said drainage tube to said inlet of said drainage bag, said first oligodynamically active tubular member precluding bacteria from ascending from said drainage bag, and a second oligodynamically active tubular member connected to said outlet of said drainage bag and oligodynamically preventing entry of bacteria from the ambient atmosphere.

* * * * *